US00PP14433P39

(12) United States Plant Patent
Weeks

(10) Patent No.: US PP14,433 P3
(45) Date of Patent: Dec. 30, 2003

(54) HYBRID TEA ROSE PLANT NAMED 'WEZGREY'

(50) Latin Name: *Rosa hybrida*
Varietal Denomination: cv. Wezgrey

(75) Inventor: O. L. Weeks, Chino, CA (US)

(73) Assignee: CP (Delaware), Inc., Wilmington, DE (US)

( * ) Notice: Subject to any disclaimer, the term of this patent is extended or adjusted under 35 U.S.C. 154(b) by 12 days.

(21) Appl. No.: 10/201,996

(22) Filed: Jul. 25, 2002

(65) Prior Publication Data

US 2002/0174463 P1 Nov. 21, 2002

Related U.S. Application Data

(63) Continuation of application No. 09/756,731, filed on Jan. 10, 2001, now abandoned.

(51) Int. Cl.[7] ..... A01H 5/00
(52) U.S. Cl. ..... Plt./132
(58) Field of Search ..... Plt./132

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct variety of Hybrid Tea rose plant is provided which forms attractive double blossoms that are a blend of soft white and lavender. The plant exhibits an upright, vigorous and uniform growth habit, dense medium green foliage, and good disease resistance. The attractive medium green foliage contrasts nicely with the light-colored blossoms. The new plant growth commonly assumes a burgundy appearance. The new variety is particularly well suited for growing as attractive ornamentation in the landscape such as in parks and gardens. Cut flower production also is possible.

7 Drawing Sheets

Figure 1:
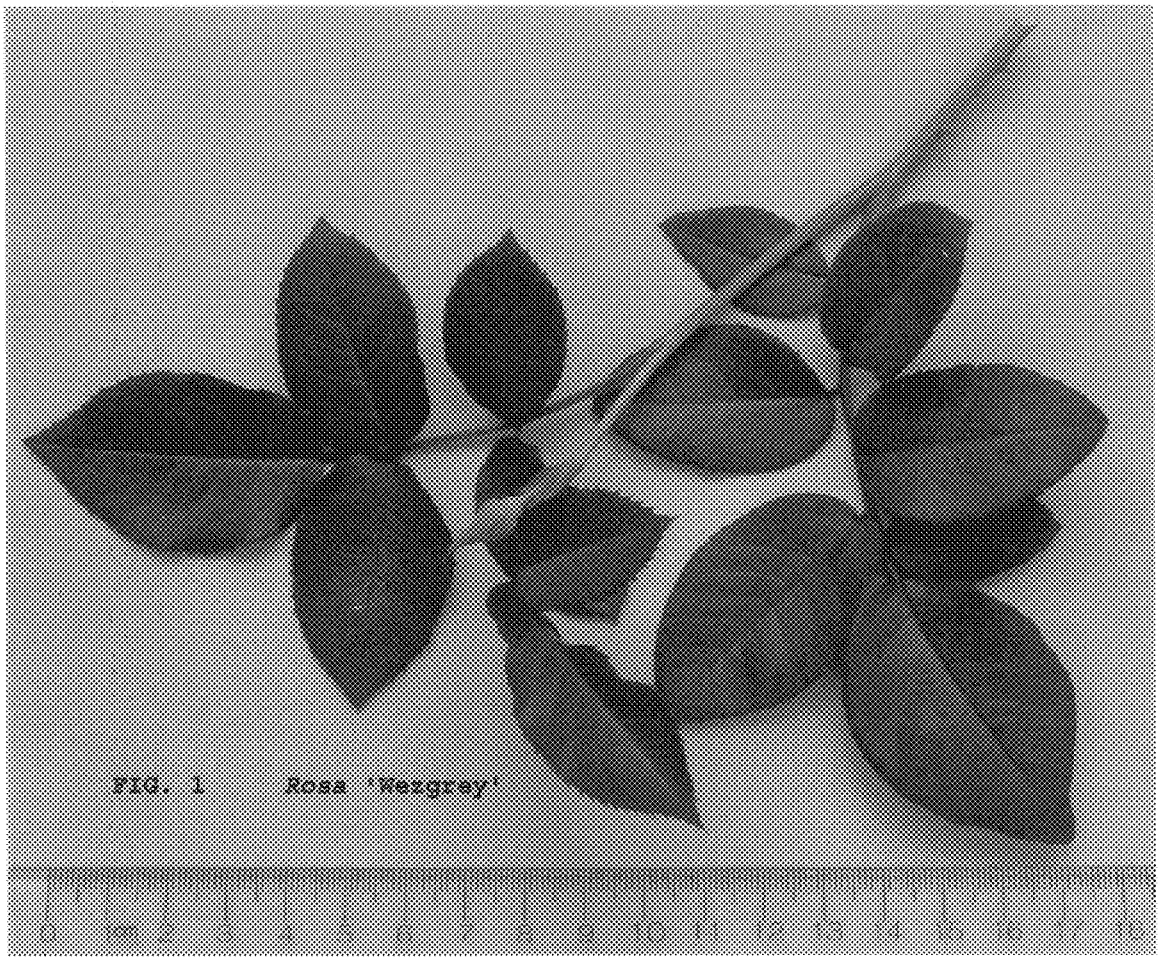

Botanical/commercial classification: *Rosa hybrida*/Hybrid Tea Rose Plant.
Varietal denomination: cv. 'Wezgrey'.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) of the new variety was the 'Silver Spoon' variety (non-patented in the United States). The male parent (i.e., the pollen parent) was the 'Wezip' variety (U.S. Plant Pat. No. 4,552). The 'Wezip' variety is marketed under the PARADISE trademark. The parentage of the new variety can be summarized as follows:

'Silver Spoon'×'Wezip'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) exhibits an upright, vigorous and uniform growth habit, (b) forms attractive double blossoms that are a blend of soft white and lavender, (c) forms dense medium green semi-glossy foliage that contrasts well with the light-colored blossoms, (d) exhibits good disease resistance, and (e) is particularly well suited for growing as attractive ornamentation.

The new variety well meets the needs of the horticultural industry and can be grown to advantage for cut flower production, as a specimen plant, or in a mass planting.

The new variety of the present invention can be readily distinguished from its ancestors. More specifically, the new Hybrid Tea rose plant forms blossoms that are a blend of soft white and lavender having approximately 26 petals on average and a moderate fruity fragrance. The 'Silver Spoon' variety forms blossoms of a mauve blend without fragrance having approximately 35 petals on average. The 'Wezip' variety forms silvery lavender blossoms with a ruby-red margin having approximately 28 petals on average.

The new variety has been found to undergo asexual propagation by a number of routes, including budding, grafting, and cuttage. Asexual propagation by the above-mentioned techniques at Wasco, Calif. has shown that the characteristics of the new variety are stable and are strictly transmissible by such asexual propagation from one generation to another.

The new variety has been named the 'Wezgrey' variety. The new variety is being marketed under the WORLD WAR II MEMORIAL ROSE trademark.

BRIEF DESCRIPTION OF THE PHOTOGRAPHS

The accompanying photographs show as nearly true as it is reasonably possible to make the same, in color illustrations of this character, typical specimens of the plant parts of the new variety. The rose plants of the new variety were three years of age and were observed during July while growing in containers on 'Dr. Huey' rootstock at West Grove, Pa. The containers were present in an open unheated growing hut. Dimensions in centimeters are indicated at the bottom of each photograph except FIG. 4.

Figures 2, 3:
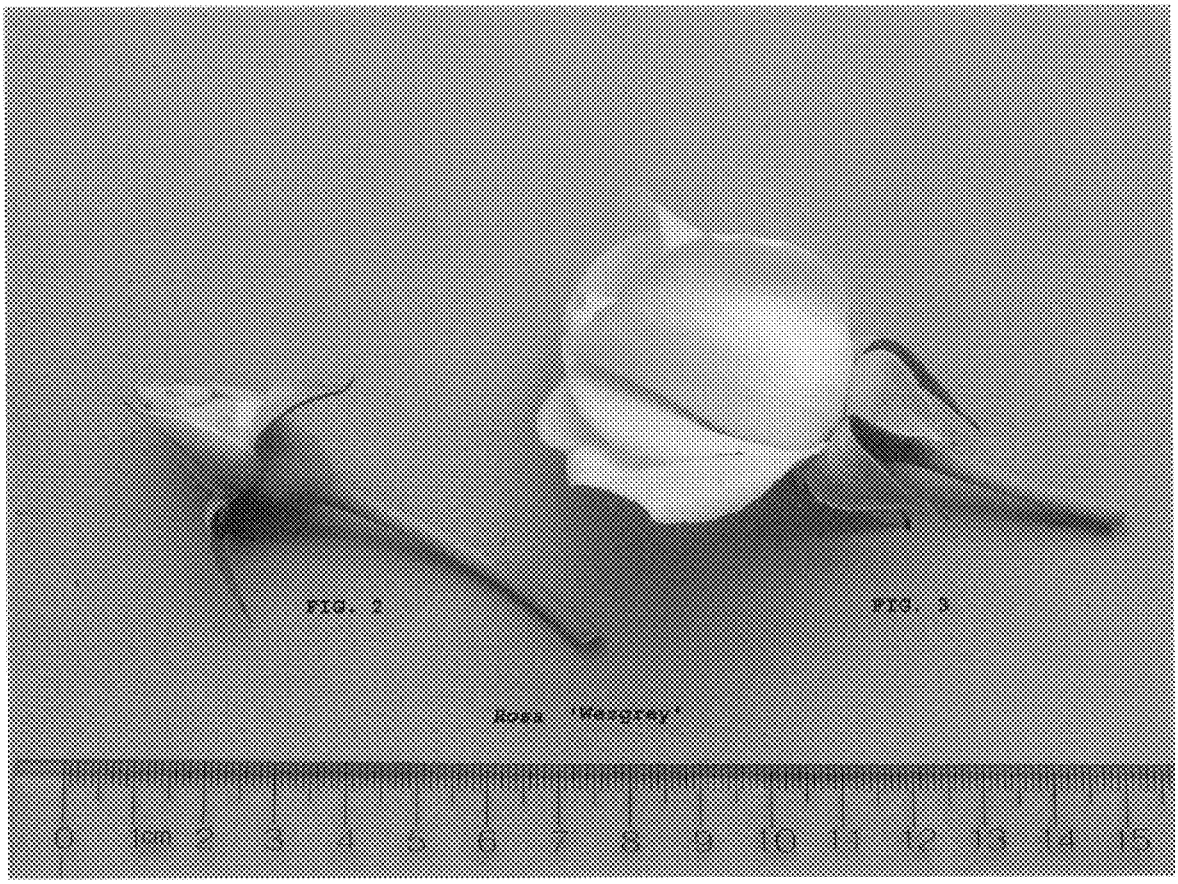
Figure 4:
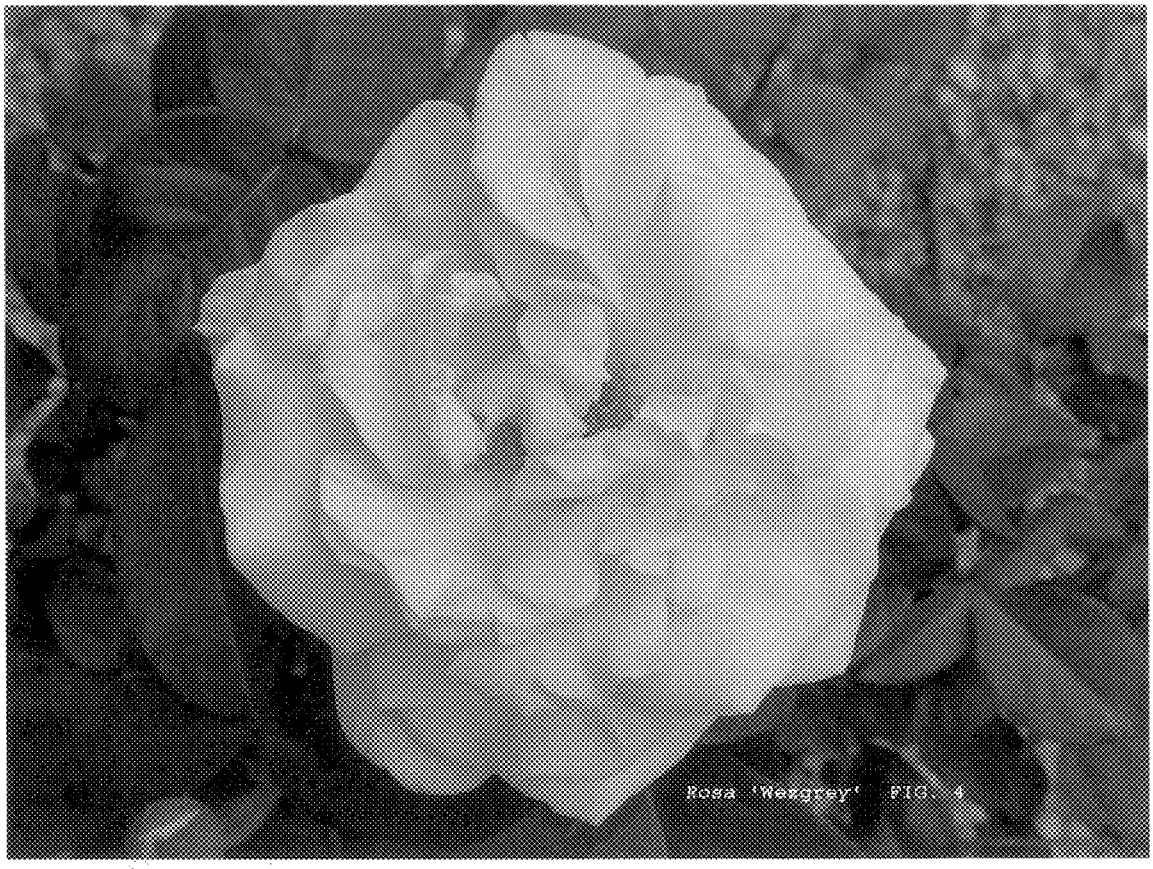
Figures 5, 6:
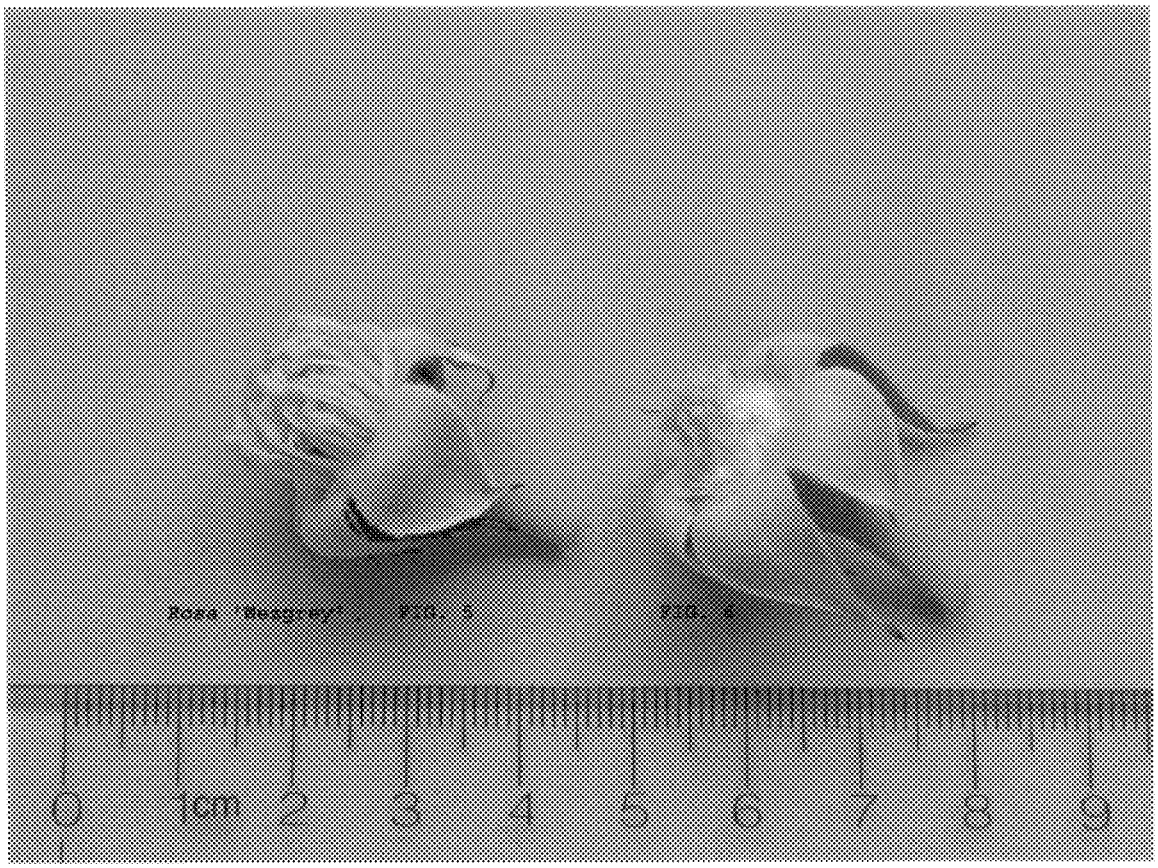
Figures 3, 4:
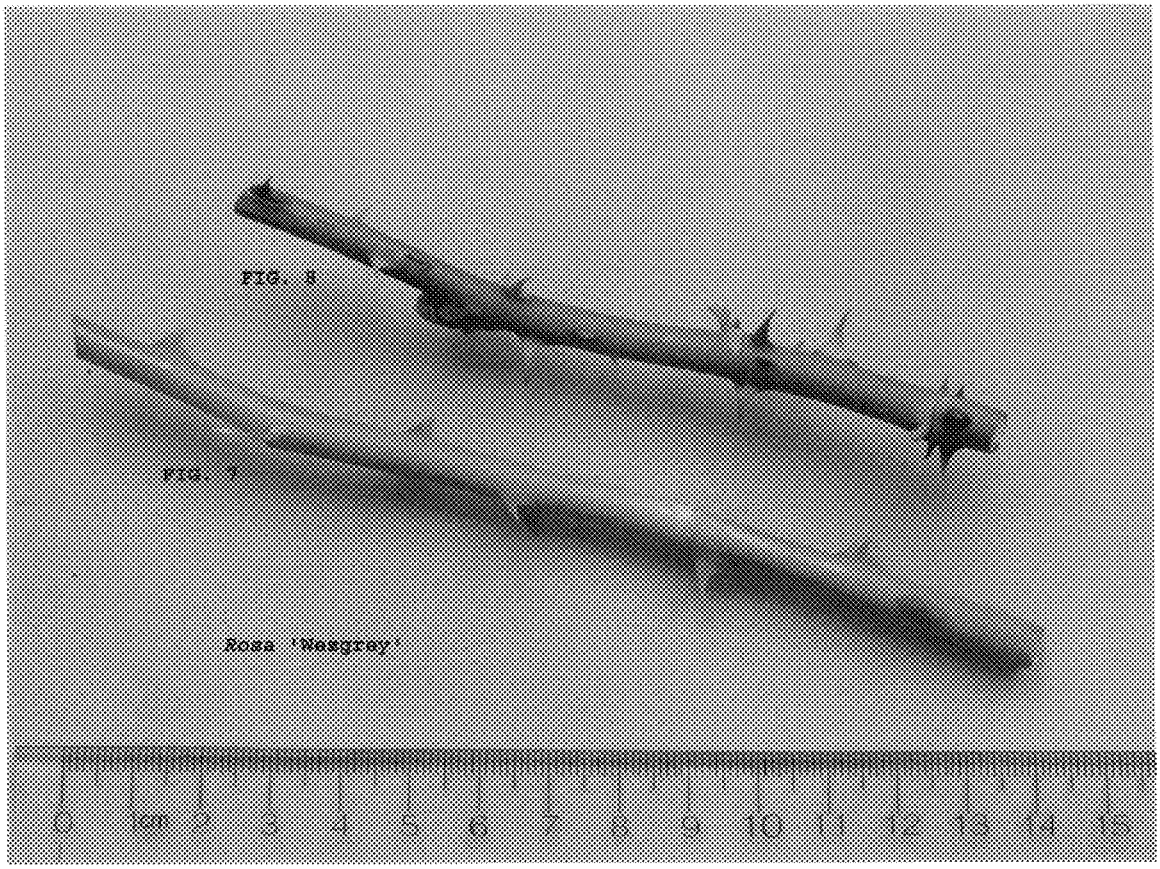
Figures 9, 10:
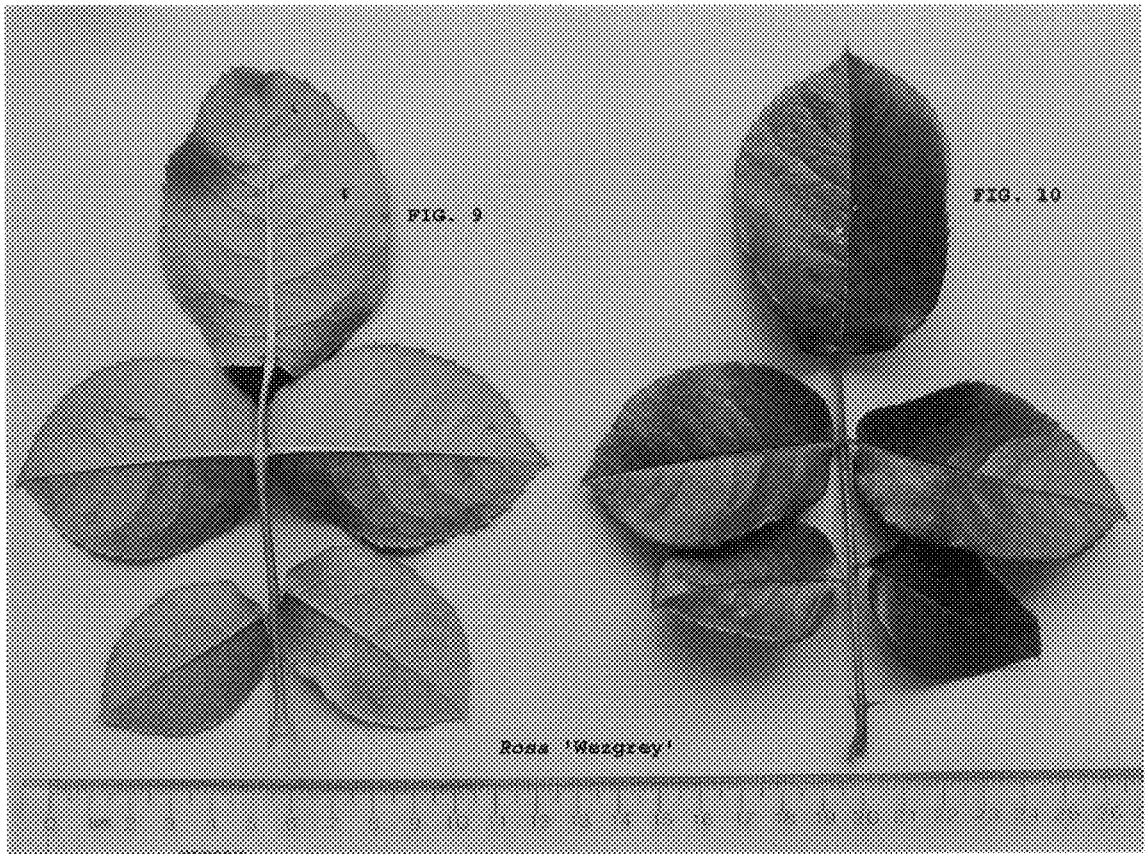
Figure 11:
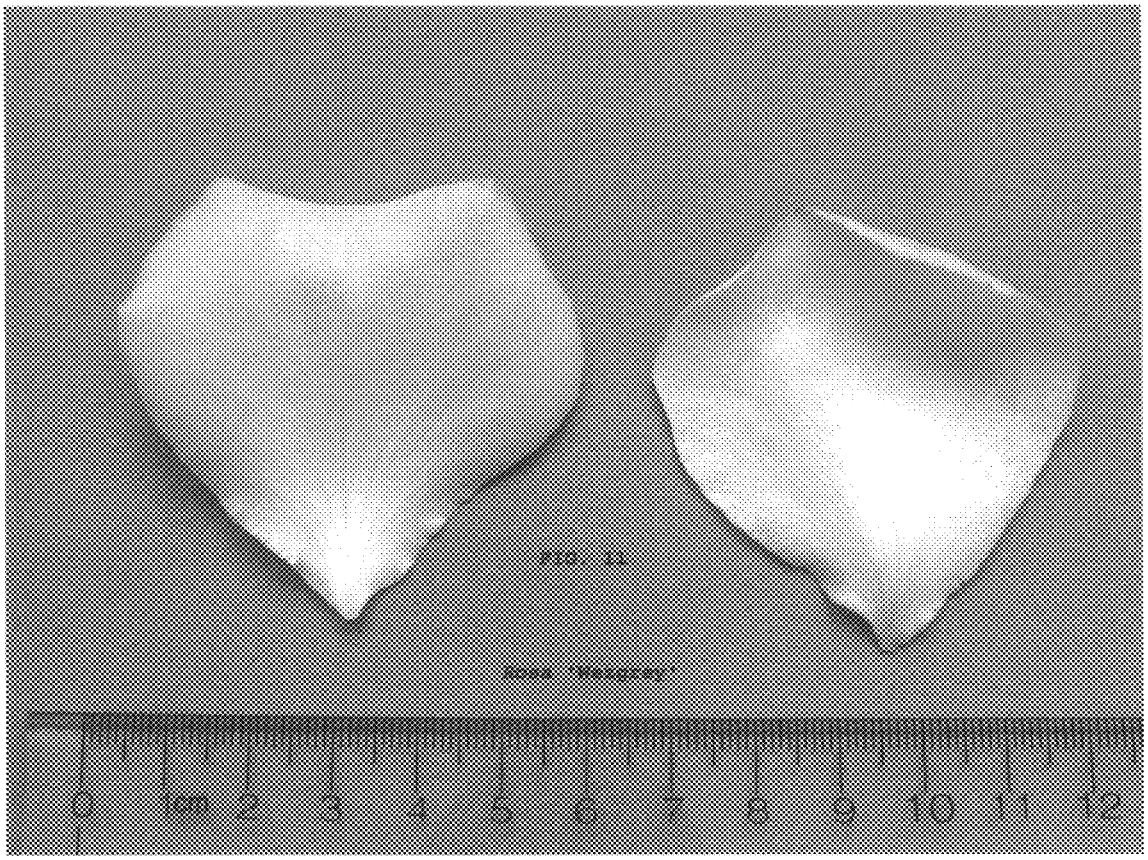

FIG. 1—illustrates a specimen of a young shoot;

FIG. 2—illustrates a specimen of a floral bud at the opening of the sepals;

FIG. 3—illustrates a specimen of a flower in the course of opening;

FIG. 4—illustrates a specimen of an open flower—plan view—obverse;

FIG. 5—illustrates a specimen of a floral receptacle showing the arrangement of the stamens and pistils;

FIG. 6—illustrates a specimen of a floral receptacle showing the arrangement of the pistils (stamens removed);

FIG. 7—illustrates a specimen of a flowering stem with foliage;

FIG. 8—illustrates a specimen of a main branch;

FIG. 9—illustrates a specimen of a leaf with five leaflets—plan view—under surface;

FIG. 10—illustrates a specimen of a leaf with five leaflets—plan view—upper surface; and FIG. 11—illustrates a specimen of maturing petals with upper surface at the left and the under surface at the right.

DETAILED DESCRIPTION

The chart used in the identification of the colors is that of The Royal Horticultural Society (R.H.S. Colour Chart—1986). The description is based on the observation of two year-old plants during October while growing on their own roots outdoors at Wasco, Calif. Color terminology is to be accorded its ordinary dictionary significance.

Class: Hybrid Tea.

Plant:

*Height.*—Approximately 4 feet at the end of the growing season.

*Width.*—Approximately 2 feet at the end of the growing season.

*Habit.*—Upright.

Branches:

*Color.*—Young stems: slightly glaucescent, Yellow-Green Group 144A and shading to 144C. Adult wood: Yellow-Green Group 146B.

*Diameter.*—Stems commonly are approximately 12 to 14 mm in diameter at the end of the growing season.

*Prickles.*—Size: approximately 5 mm in length on average. Quantity: moderately numerous, approximately 15 true thorns plus bristles on a stem having a length of 30 cm. Color: Near Yellow-Green Group 144A and 144B with a slight greyed-orange tint on when present young stems, and Greyed-Orange Group 173D near the base and shading to near and through Greyed-Orange Group 174B to 174D, and at the tip near Greyed-Orange Group 174A on mature stems of current-season growth. Shape: nearly straight to slightly convex on the upper side and concave on the under side.

Leaves:

*Stipules.*—Narrow, triangular, and with auricle facing outwards.

*Petioles.*—Upper surface: Yellow-Green Group 144C, commonly with scattered minute stiff glandular hairs. Under surface: Yellow-Green Group 144A, and typically glabrous, but may sometimes bear 1 or 2 prickles that are curved and approximately 1.8 mm in length. Size: approximately 33 mm in length on average and approximately 2 mm in diameter on average when present with a five-leaflet leaf.

*Rachis.*—The upper surface commonly has scattered minute stiff glandular hairs that average approximately 0.3 mm in length, and commonly bears approximately 1 to 6 pronounced prickles per leaf that are up to approximately 2.5 mm in length.

*Size.*—A typical five-leaflet leaf commonly is approximately 12 to 17 cm. (average approximately 15 cm) in length and approximately 11 to 11.5 cm (average approximately 11.1 cm) in width.

*Leaflets.*—Number: 3, 5, and 7. Shape: ovate with serrate margins, rounded base and acute apices. Size: the terminal leaflets of five-leaflet leaves commonly are approximately 58 to 75 mm (average approximately 69 mm) in length, and approximately 43 to 55.5 mm (average approximately 51 mm) in width. Serration: regular. Texture: glabrous and glaucescent for younger foliage, thinly to moderately coriaceous for mature foliage. General appearance: dense, leathery, medium green, and with a semi-glossy finish. Color (young foliage): Upper surface: near Greyed-Purple Group 187A and shading towards Purple Group 79A. Under surface: primarily Greyed-Purple Group 183D with shading of Greyed-Purple Group 183B and 183C, and 184A and 184B. Color (adult foliage): Upper surface: near Green Group 137A with shading to Green Group 139A. Under surface: near Greyed-Green Group 191A. Venation pattern: pinnately reticulated. Venation color: on the upper surface near Green Group 143A and 143B, and on the lower surface near and through Green Group 139D and Greyed-Green Group 193A.

Inflorescence:

*First bud burst.*—Commonly April 7th to 15th at Wasco, Calif., and commonly June 7th to 15th at West Grove, Pa.

*Flowering duration.*—More or less continuously, though the number of open flowers on the plant may vary throughout the season.

*Number of flowers.*—Usually one to three flowers per stem.

*Peduncle.*—Yellow-Green Group 144B with prickles near Greyed-Purple Group 185B, approximately 3 mm in diameter, and the length is approximately 6 cm on average.

*Sepals.*—Upper surface: near Yellow-Green Group 144C with pubescence of White Group 155D. Under surface: Yellow-Green Group 144C with some extensions. Number: five. Size: commonly approximately 20 to 25 mm (average approximately 23.2 mm) in length, and approximately 10 to 11.5 mm (average approximately 10.4 mm) in width at the widest point. Color: Yellow-Green Group 144B to 144C.

*Buds.*—Shape: pointed. Size: large. Length: approximately 3 cm on average. Diameter: approximately 1.6 cm when sepals first separate. Color upon opening: Upper surface: Yellow-Green Group 150D with highlights of Purple Group 75D. Under surface: Yellow-Green Group 150D.

*Flower.*—Shape: double and high-centered. Diameter: approximately 7 cm on average. Color (when opening begins): Upper surface: near White Group 155A and 155B. Under surface: combination of Red Group 56D and White Group 155A. Color (when blooming): Upper surface: near White Group 155A with pinkish-lavender tones towards the margins. Under surface: near White Group 155D with pinkish-lavender tones towards the margins. Color (at the end of opening): Upper surface: near White Group 155A with pinkish-lavender tones towards the margins. Under surface: near White Group 155D with pinkish-lavender tones towards the margins. The specified pinkish-lavender tones for both surfaces are present as broad diffuse areas of varying intensity becoming more pronounced as the blossoms mature and are subtle in their presentation. Such tones commonly are Red-Purple Group 62D and Purple Group 75D. Fragrance: present. Petal shape: orbicular. Petal margin: mostly entire and smooth near the base, becoming somewhat repandos towards the apex, and with a pronounced tendency to recurve outwards. The central portion of the mid-range petals tends to be incised at the apex and the interior petals commonly display substantial crinkling. Petal apex: broadly obtuse to slightly retuse. Petal base: broadly cuneate. Petal texture: glabrous and minimally coriaceous. Petal number: approximately 20 to 32 (approximately 26 on average). Flower longevity: a typical flower commonly lasts approximately 5 to 7 days from bud crack to petal drop on the plant, and approximately 3 to 5 days when cut and placed in a vase. Stamen number: approximately 85 on average. Anthers: near Yellow-Orange Group 16B in coloration. Filaments: near Yellow-White Group 158B in coloration. Pistils: approximately 40 on average. Stigmas: near Yellow-Orange Group 18B in coloration. Styles: near Yellow-Orange Group 18A in coloration. Receptacle: separate and free with achenes on the bottom and the wall. Hips: none observed during observations to date.

Development:

*Vegetation.*—Vigorous and uniform.

*Blooming.*—Mostly single blooms and sometimes in clusters.

*Resistance to diseases.*—Good.

*Hardiness.*—Performs well in U.S.D.A. Hardiness Zone No. 7. With some protection can be grown in Zone No. 6.

Plants of the 'Wezgrey' variety have not been observed while being grown under all possible environmental conditions. Thus, the phenotypic expression may vary somewhat with different light intensity and duration, and different cultural and environmental conditions.

I claim:

1. A new and distinct variety of Hybrid Tea rose plant characterized by the following combination of characteristics:

(a) exhibits an upright, vigorous and uniform growth habit, (b) forms attractive double blossoms that are a blend of soft white and lavender, (c) forms dense medium green semi-glossy foliage that contrasts well with the light-colored blossoms, (d) exhibits good disease resistance, and (e) is particularly well suited for growing as attractive ornamentation;

substantially as herein shown and described.

* * * * *

FIG. 1 *Rosa* 'Rexgrey'

Rose "Monsieur"

Rosa 'Wazgrey' FIG. 4

Rosa 'Meagrey'

0
1cm
2
3
4
5
6
7
8
9

Rosa 'Weggrey'
0 1 2 3 4 5 6 7 8 9 10 11 12 13 14 15

Rosa 'Wezgrey'

UNITED STATES PATENT AND TRADEMARK OFFICE

CERTIFICATE OF CORRECTION

PATENT NO. : PP 14,433 P3
DATED : December 30, 2003
INVENTOR(S) : O. L.Weeks

It is certified that error appears in the above-identified patent and that said Letters Patent is hereby corrected as shown below:

Title page,
Insert the following under Item [73], Assignee,
-- (*) Notice: Subject to any disclaimer, the term of this patent is extended or adjusted under 35 U.S.C § 154(b) by 12 days. --

Signed and Sealed this

Twentieth Day of April, 2004

JON W. DUDAS
*Acting Director of the United States Patent and Trademark Office*